United States Patent
Grit

(10) Patent No.: US 9,776,021 B2
(45) Date of Patent: Oct. 3, 2017

(54) ANHYDROUS DYEING COMPOSITION AND PROCESS FOR DYEING HAIR

(71) Applicant: KAO GERMANY GMBH, Darmstadt (DE)

(72) Inventor: Mustafa Grit, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 51 days.

(21) Appl. No.: 14/898,637

(22) PCT Filed: Dec. 13, 2013

(86) PCT No.: PCT/EP2013/076476
§ 371 (c)(1),
(2) Date: Dec. 15, 2015

(87) PCT Pub. No.: WO2015/188841
PCT Pub. Date: Dec. 17, 2015

(65) Prior Publication Data
US 2016/0199291 A1    Jul. 14, 2016

(30) Foreign Application Priority Data

Dec. 21, 2012 (EP) .................................... 12198986

(51) Int. Cl.
| | |
|---|---|
| *A61Q 5/10* | (2006.01) |
| *A61K 8/31* | (2006.01) |
| *A61K 8/34* | (2006.01) |
| *A61K 8/36* | (2006.01) |
| *A61K 8/41* | (2006.01) |
| *A61K 8/49* | (2006.01) |
| *A61K 8/58* | (2006.01) |
| *A61K 8/39* | (2006.01) |
| *A61K 8/42* | (2006.01) |
| *A61K 8/46* | (2006.01) |
| *A61K 8/86* | (2006.01) |
| *A61K 8/92* | (2006.01) |

(52) U.S. Cl.
CPC ................. *A61Q 5/10* (2013.01); *A61K 8/31* (2013.01); *A61K 8/347* (2013.01); *A61K 8/361* (2013.01); *A61K 8/39* (2013.01); *A61K 8/415* (2013.01); *A61K 8/42* (2013.01); *A61K 8/463* (2013.01); *A61K 8/494* (2013.01); *A61K 8/585* (2013.01); *A61K 8/86* (2013.01); *A61K 8/922* (2013.01); *A61K 2800/31* (2013.01); *A61K 2800/4324* (2013.01); *A61K 2800/882* (2013.01)

(58) Field of Classification Search
CPC .......... A61Q 5/10; A61K 8/494; A61K 8/463; A61K 8/42; A61K 8/361; A61K 8/585; A61K 8/347; A61K 8/415; A61K 2800/4324; A61K 2800/882
See application file for complete search history.

(56) References Cited

U.S. PATENT DOCUMENTS

| | | | | |
|---|---|---|---|---|
| 5,641,480 A | * | 6/1997 | Vermeer | A61K 8/046 424/70.1 |
| 2004/0181883 A1 | * | 9/2004 | Legrand | A61K 8/31 8/405 |
| 2009/0229059 A1 | * | 9/2009 | Cremer | A61K 8/49 8/405 |
| 2010/0186177 A1 | * | 7/2010 | Hercouet | A61K 8/31 8/408 |
| 2010/0275387 A1 | | 11/2010 | Charrier et al. | |
| 2010/0299847 A1 | * | 12/2010 | Cohen | A61K 8/19 8/408 |

FOREIGN PATENT DOCUMENTS

| CA | 2 481 140 A1 | 3/2006 |
|---|---|---|
| EP | 2 198 842 A2 | 6/2010 |

OTHER PUBLICATIONS

STIC Search Report dtaed Aug. 2, 2016.*
International Search Report and Written Opinion of the ISA dated Sep. 24, 2015, mailed Oct. 6, 2015.

* cited by examiner

*Primary Examiner* — Eisa Elhilo
(74) *Attorney, Agent, or Firm* — Norris McLaughlin & Marcus PA

(57) ABSTRACT

The present invention relates to an anhydrous liquid dyeing composition comprising one or more oil liquid at 20° C., one or more oxidative dye precursor, at least one anionic and at least one nonionic surfactant for achieving intensive homogeneous colors on hair.

18 Claims, No Drawings

ANHYDROUS DYEING COMPOSITION AND PROCESS FOR DYEING HAIR

This application is a §371 U.S. National stage of PCT International Patent Application No. PCT/EP2013/076476, filed Dec. 13, 2013, which claims foreign priority benefit of European Patent Application No. EP 12198986.7, filed Dec. 20, 2012, the disclosures of each of which patent applications are incorporated herein by reference.

The present invention relates to an anhydrous liquid dyeing composition comprising one or more oil, one or more oxidative dye precursor and one or more surfactant for achieving intensive homogeneous colors on hair.

Oxidative hair coloring has been known for many decades. It is the preferred way of hair coloring especially when to be colored hair comprises in a certain extent grey hair. Furthermore, it is also one of the commonly used dyeing practices when hair comprises various parts with various degree of damage due to previous chemical and/or environmental effects. Such hair on one hand is difficult to color intensively and homogeneously and on the other hand does show different degree of dyestuff retention and therefore raises difficulties in daily hair color practice. There have been many attempts to solve such problems; however, there is still quite high requirement for further improvements.

The present invention starts from the above problems and aims at providing an oxidative hair dyeing composition which delivers homogeneous and long lasting intensive colors especially to a hair comprising parts with different degree of damage form previous chemical and/or environmental effects.

It has been unexpectedly and surprisingly found out that an anhydrous liquid dyeing composition which is liquid at 20° C. comprising one or more oxidative dye precursors, optionally one or more coupling substances, one or more oil which is liquid at 20° C., at least one anionic surfactant and at least one nonionic surfactant delivers intensive homogeneous and long lasting colors to human hair.

Accordingly the first object of the present invention is an anhydrous dyeing composition for hair which is liquid at 20° C. comprising one or more oxidative dye precursors, optionally one or more coupling substances, one or more oil liquid at 20° C., at least one anionic surfactant and at least one nonionic surfactant.

With the term liquid it is meant that the composition and the oil are liquid at 20° C.

The second object of the present invention is the use of the composition of the present invention for dyeing hair.

The third object of the present invention is a process for dyeing hair wherein the composition of the present invention is mixed with two aqueous compositions wherein on of the compositions is an aqueous oxidizing composition comprising at least one oxidizing agent and having a pH in the range of 2 to 6 and the second aqueous composition comprises at least one alkalizing agent wherein the mixture thus obtained is an emulsion, preferably an oil in water emulsion and applied onto hair and after leaving on the hair 5 to 45 min, rinsed off from hair and the hair is optionally shampooed.

The fourth object of the present invention is kit for dyeing hair which comprises two or more compositions wherein one of the compositions is the composition of the present invention, the second composition is an aqueous composition comprising one or more oxidizing agent and preferably a third aqueous composition comprising one or more alkalizing agent.

The composition of the present invention comprises one or more oil which is liquid at 20° C. Total concentration of one or more oil is in the range of 35 to 80%, preferably 40 to 75%, more preferably 45 to 70% and most preferably 45 to 60% by weight, calculated to the total composition.

One or more oil may be selected from synthetic and natural oils. Synthetic oils are silicones especially those of nonvolatile ones such as dimethicones with viscosity of 50 to 350 cSt measured by capillary viscosimeter and at 20° C., fatty acid fatty alcohol esters according to the general structure

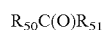

$R_{50}C(O)R_{51}$ wherein $R_{50}$ is a straight or branched, saturated or unsaturated alkyl with 11 to 21 C atomes and $R_{51}$ is a straight or branched, saturated or unsaturated alkyl with 1 to 22 C atomes such as behenyl behenate, behenyl isostearte, butyl stearate, butyl oleate, butyl myristate, butyloctyl oleate, cetyl palmitate, cetyl myristate, cetyl oleate, cetyl caprylate, cetyl caprate, decyl oleate, decyl cocoate, decyl isostearate, ethylhexyl myristate, ethyl hexyl laurate, ethyl hexyl oleate, ethyl isostearte, ethyl laurate, ethyl linoleate, ethyl myristate, ethyl oleate, ethyl palmitate, ethylricinoleate, ethyl stearate, hexyl isostearet, hexyl laurate, hexyl myristate, hexyl stearate, hexyl decyl oleate, isobutyl laurate, isobutyl myristate, isobutyl palmitate, isobutyl stearate, isocetyl behenate, isobutyl laurate, isobutyl oleate, isobutyl stearate, isobutyl cocoate, isohexyl caprate, isopropyl palmitate, isopropyl stearate, isopropyl behenate, isopropyl laurate, isopropyl oleate, isopropyl ricinoleate and isopropyl palmitate, and fatty alcohol ethers according to general structure

$R_3OR_4$ wherein $R_3$ and $R_4$ are same or different, straight or branched, saturated or unsaturated alkyl with 8 to 22 C atoms such as dicetyl ether, dimyristyl ether, dicyprylyl ether and dodecyl ether.

Natural oils are mineral oil and plant derived triglycerides such as ricinus oil, soja oil avocado oil, olive oil, almond oil, peach oil, passiflora oil, black cumin oil, borage oils, evening primrose oil, grape seed oil, hempseed oil, kukui nut oil, rosehip oil, safflower oil, walnut oil and wheat germ oil.

In a preferred embodiment of the present invention, the anhydrous composition comprises at least one synthetic oil and at least one natural oil.

The anhydrous composition of the present invention comprises at least one anionic surfactant.

Non-limiting suitable examples to anionic surfactants are especially the known alkyl sulphates and alkyl ether sulfates, carboxylic acids, in particular in form of their alkali salts, as well as protein fatty acid condensates, fatty acid salts, alkyl/alkenyl succinates, anionic amino acid surfactants especially glutamates such as sodium lauroyl glutamate. The preferred anionic surfactants are alkyl sulphates and alkyl ether sulphates and their mixtures. Examples to the alkyl sulfates and their salts such as ammonium C12-15 alkyl sulphate, ammonium C12-16 alkyl sulphate, ammonium coco sulphate, ammonium lauryl sulphate, ammonium myristyl sulphate, magnesium coco sulphate, magnesium lauryl sulphate, magnesium coco/TEA sulphate, MEA lauryl sulphate, MIPA lauryl sulphate, potassium lauryl sulphate, sodium caprylyl sulphate, sodium cetearyl sulphate, sodium cetyl sulphate, sodium coco sulphate, sodium decyl sulphate, sodium ethylhexyl sulphate, sodium lauryl sulphate, sodium myristyl sulphate, sodium oleyl sulphate, sodium stearyl sulphate, sodium tridecyl sulphate, TEA coco sulphate, TEA lauryl sulphate, TEA oleyl sulphate and TIPA lauryl sulphate and their mixtures. Examples to alkyl ether sulphates are ammonium coceth sulphate, ammonium laureth sulphate, ammonium myristeth sulphate, magnesium coceth sulphate, magnesium laureth sulphate, MEA laureth sulphate, MIPA laureth sulphate, potassium laureth sulphate, ceteareth sulphate, sodium ceteth sulphate, sodium coceth sulphate, sodium laureth sulphate, sodium myristeth sulphate, sodium oleth sulphate, sodium steareth sulphate, sodium trideceth sulphate, TEA coceth sulphate, TEA laureth sulphate, TEA oleeth sulphate and TIPA laureth sulphate and their mixtures. Among those sodium lauryl sulphate and sodium laureth sulphate are the most preferred ones.

The anhydrous composition of the present invention comprises at least one nonionic surfactant.

Suitable nonionic surfactants are in particular fatty alcohol polyglycol ethers according to general structure $$R_{52}(OCH_2CH_2)_nOH$$

wherein $R_{52}$ is straight or branched, saturated or unsaturated alkyl with 8 to 22 C atoms and n is a number between 1 and 50, preferably 5 and 50, and more preferably 10 and 40 and most preferably 10 and 30.

Suitable non-limiting examples to non-ionic surfactants of fatty alcohol polyglycol ethers are laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-21, laureth-23, laureth-25, laureth-30, laureth-38, laureth-40, laureth-50, ceteth-1, ceteth-2, ceteth-3, ceteth-4, ceteth-5, ceteth-6, ceteth-7, ceteth-10, ceteth-12, ceteth-13, ceteth-14, ceteth-15, ceteth-16, ceteth-17, ceteth-18, ceteth-18, ceteth-20, ceteth-23, ceteth-24, ceteth-25, ceteth-30, ceteth-40, ceteth-45, isoceteth-5, isoceteth-7, isoceteth-10, isoceteth-12, isoceteth-15, isoceteth-20, isoceteth-25, isoceteth-30, isosteareth-2, isosteareth-3, isosteareth-5, isosteareth-8, isosteareth-10, isosteareth-12, isosteareth-15, isosteareth-18, isosteareth-20, isosteareth-22, isosteareth-25, isosteareth-50, steareth-1, steareth-2, steareth-3, steareth-4, steareth-5, steareth-6, steareth-7, steareth-8, steareth-10, steareth-11, steareth-12, steareth-13, steareth-14, steareth-15, steareth-16, steareth-20, steareth-21, steareth-25, steareth-27, steareth-30, steareth-40, steareth-50, ceteareth-2, ceteareth-2, ceteareth-2, ceteareth-2, ceteareth-2, ceteareth-2, ceteareth-2, ceteareth-3, ceteareth-4, ceteareth-5, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, beheneth-2, beheneth-5, beheneth-10, beheneth-15, beheneth-20, beheneth-25, beheneth-30, oleth-2, oleth-3, oleth-4, oleth-5, oleth-6, oleth-7, oleth-8, oleth-9, oleth-10, oleth-11, oleth-12, oleth-15, oleth-16, oleth-20, oleth-23, oleth-24, oleth-25, oleth-30, oleth-35, oleth-40, oleth-44, oleth-45 and oleth-50 and their mixtures.

Further suitable non-ionic surfactants are fatty acid alkanolamides, amineoxides, and especially $C_8$-$C_{18}$-alkyl polyglucosides of the general structure $$R_6-O-(R_7O)_n-O-Z_x$$

wherein $R_6$ is an alkyl group with 8 to 18 carbon atoms, $R_7$ is an ethylene or propylene group, Z is a saccharide group with 5 to 6 carbon atoms, n is a number from 0 to 10 and x is a number between 1 and 5. Examples are decyl polyglucoside and cocoyl polyglucoside, both being commercially available.

Further suitable and preferred non-ionic surfactants are fatty acid mono or dialkanolamides of the general structure $$R_{60}C(O)NR_{61}R_{62}$$

wherein $R_{60}$ is straight or branched, saturated or unsaturated alkyl with 9 to 21 C atomes, $R_{61}$ and $R_{62}$ are same or different H and C1 to C4 alkyl substituted with an OH group which may additionally be branched.

Suitable examples to the fatty acid mono or dialkanolamides are cocamide DEA, cocamide DIPA, cocamide MEA, cocamide MIPA, lauramide DEA, lauramide DIPA, lauramide MEA, lauramide MIPA, myristamide DEA, myristamide DIPA, myristamide MEA, myristamide MIPA, oleamide DEA, oleamide DIPA, oleamide MEA, oleamide MIPA, soyamide DEA, stearamide DEA, stearamide MEA, stearamide DIPA, stearamide MIPA, behenamide DEA, behenamide MEA, behenamide DIPA and behenamide MIPA.

Among non-ionic surfactants ethoxylated fatty alcohols and mono or dialkanolamides are the most preferred ones.

Total concentration of the anionic and non-ionic surfactants varies in the range of 2% to 40%, preferably 5 to 35%, more preferably 7.5 to 30 and most preferably 10% to 30% by weight, calculated to total composition.

The compositions may comprise further surfactants such as cationic surfactants especially mono alkyl quaternary ammonium salts of the following general structure

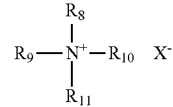

where $R_8$ is a saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 1-4 or $$R_{13}COO(CH_2)_n$$

where $R_{13}$ is saturated or unsaturated, branched or non-branched alkyl chain with 7-21 C atoms and n has typical value of 1-4, and
and $R_9$, $R_{10}$ and $R_{11}$ are independent from each other H or lower alkyl chain with 1 to 4 carbon atoms, and X is an anion such as chloride, bromide or methosulfate.

Suitable non-limiting examples are cetrimonium chloride, steartrimonium chloride and behentrimonium chloride.

The anhydrous composition of the present invention comprises one or more oxidative dye precursors.

Suitable examples to the oxidative dye precursors are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethylaminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5- diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2((3-hydroxyethyl amino)-6-methoxypyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof.

Further, indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

Suitable coupling agents are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl) amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. 5-amino-2-methylphenol, 2-methyl-5-hydroxyethylaminophenol, 2,4-diamnophenoxyethanol, 2-amino-4-hydroxyethylaminoanisol, 2-methyl-5-amino-6-chlorophenol, 1,3-bis(2,4-diaminophenoxy)propane, 2-bis(2-hydroxyethyl)aminotoluene, 2-amino-5-methylphenol or the water-soluble salts thereof.

Concentration of one or more oxidative dyes in total—total concentration of precursors and couplers, if present—is in the range of 0.001 to 20% by weight, preferably 0.01 to 15% more preferably 0.05 to 12.5%, most preferably 0.1 to 10%, in particular 0.1 to 7.5% by weight calculated to the total composition.

In a still further embodiment of the present invention, the anhydrous composition of the present invention comprises one or more direct dyes. Suitable direct dyes are selected from cationic, anionic, neutral nitro dyes and their mixtures. Preferred are cationic and neutral nitro dyes and their mixtures.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 10% by weight, preferably 0.01 to 7.5% more preferably 0.05 to 5%, most preferably 0.1 to 3% by weight calculated to total composition.

The anhydrous composition of the present invention preferably comprises one or more polyol at a concentration in the range of 0.1 to 10%, preferably 0.5 to 7.5%, more preferably 0.75 to 5% and most preferably 1 to 5% by weight calculated to the total of the composition. The term polyol means any compound having 2 or more hydroxyl groups in its molecule. Suitable non-limiting examples are glycerin, 1,2-propylene glycol, polyglycerins with 2 to 10 glycerin units, panthenol, glycol, butyleneglycol, 1,2-butanediol, 1,4, butanediol, 2,3-butanediol, pentylene glycol and 1,5-pentanediol. Preferred are glycerin, 1,2-propylene glycol, glycol, butyleneglycol 1,2-butanediol, 1,4, butanediol, 2,3-butanediol, and panthenol. More preferred are glycerin, 1,2-propylene glycol, glycol, butyleneglycol, and panthenol. Most preferred are glycerin, 1,2-propylene glycol, and panthenol and particularly preferred polyol is glycerin.

The anhydrous composition preferably comprises additionally a surface active block polymer of the general structure

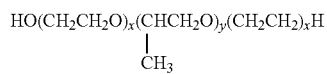

wherein x is a number 4 or more and y is a number 25 or more.

The surface active block polymers are known with CTFA name Poloxamer and commercially available under the trade name Pluronic. Suitable and preferred example is Poloxamer 101.

Concentration of surface active block polymer of the above general structure is in the range of 0.1 to 7.5%, preferably 0.2 to 5% more preferably 0.5 to 4% and most preferably 0.5 to 3% by weight calculated to the total composition.

In a further preferred embodiment of the present invention the anhydrous composition comprises one or more phospholipids also known as lecithin. Suitable ones are crude lecithin such soybean and egg yolk lecithin as well as their hydrogenated forms. Also suitable are the synthetic lecithin and especially phosphatidyl choline according to following general structure

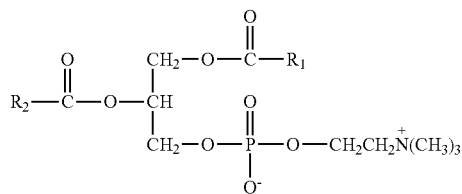

wherein R1 and R2 are same or different saturated or unsaturated, straight or branched alky chain with 11 to 21 C atoms. Suitable non-limiting examples are dimyristoylphosphatidyl choline, dipalmitylphosphatidyl choline, distearylphosphatidyl choline, dioleoylphosphatidyl choline and dilinoleoylphosphatidyl choline.

Concentration of one or more phospholipid is in the range of 0.1 to 10%, preferably 0.2 to 7.5% more preferably 0.5 to 6% and most preferably 0.5 to 5% by weight calculated to the total composition.

The anhydrous composition of the present invention is mixed with two other compositions prior to application onto hair wherein one of the compositions is an aqueous composition comprising one or more oxidizing agents. Suitable and non-limiting examples are hydrogen peroxide, urea peroxide, melamine peroxide and sodium bromate and most preferably it is hydrogen peroxide preferably at a concentration of 1 to 20%, preferably 1 to 15% and more preferably 2 to 12% by weight calculated to the total of the composition, and preferably has a pH in the range of 2 to 5, more preferably 2 to 4.

Preferably the oxidizing composition is an oil in water emulsion and comprises additionally one or more fatty alcohol and/or oil and one or more surfactants disclosed above.

The above disclosed oils are also suitable for the aqueous oxidizing composition. The concentration of oil in the aqueous oxidizing composition, if present, is in the range of 0.01 to 10%, preferably 0.1 to 5% by weight calculated to the total composition.

Suitable fatty alcohols are according to the general structure

wherein $R_{40}$ is a saturated or unsaturated, straight or branched alkyl chain having 12 to 30 C atoms which may also be substituted with one or more OH groups.

The non-limiting examples to suitable fatty alcohols are arachidyl alcohol, behenyl alcohol, brassica alcohol, C9-11 alcohols, C10-16 alcohols, C12-13 alcohols, C12-15 alcohols, C12-16 alcohols, C14-15 alcohols, C14-22 alcohols, C20-22 alcohols, caprylyl alcohol, cetearyl alcohol, cetyl alcohol, coconut alcohol, decyl alcohol, hydrogenated brassica alcohol, hydrogenated jojoba alcohol, hydrogenated rapeseed alcohol, hydrogenated tallow alcohol, hydroxystearyl alcohol, jojoba alcohol, lauryl alcohol, myristyl alcohol, oleyl alcohol, olive alcohol, palm alcohol, palm kernel alcohol, stearyl alcohol, tallow alcohol, and tridecyl alcohol and their mixtures.

Preferred are cetyl, stearyl, behenyl and cetearyl alcohols and their mixtures. The most preferred is cetearyl alcohol which is the mixture of cetyl and stearyl alcohols.

One or more fatty alcohol is used in the compositions of the present invention at a concentration 0.5 to 30%, preferably 1 to 25% more preferably 2 to 20%, most preferably 2.5 to 15% by weight calculated to the total composition.

The above disclosed surfactants for the anhydrous composition are also suitable for the aqueous oxidizing composition and preferably comprised in the range of 0.1 to 10% and more preferably 0.2 to 7.5% by weight calculated to the total composition.

The second composition mixed with the anhydrous composition of the present invention is an aqueous composition comprising one or more alkalizing agent. Suitable alkalizing agents are sodium hydroxide, ammonia or ammonium hydroxide and a compound according to the general formula

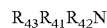

wherein $R_{43}$, $R_{41}$ and $R_{42}$ are same or different H, C1-C6 alkyl, C1-C6 monohydroxyalkyl or C2-C6 polyhydroxyalkyl with the condition that at least one of $R_{43}$, $R_{41}$ and $R_{42}$ is a mono or polyhydroxyalkyl. Preferably $R_{43}$, $R_{41}$ and $R_{42}$ are same or different H, C1-C4 alkyl, C1-C4 monohydroxyalkyl or C2-C4 polyhydroxyalkyl with the condition that at least one of $R_{43}$, $R_{41}$ and $R_{42}$ is a mono or polyhydroxyalkyl.

Suitable alkanolamines according to the general formula of above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine. Ammonia is also preferred as an alkalizing agent.

Within the meaning of the present invention it should also be understood that the alkalizing compositions and/or ready to use oxidative dyeing compositions can comprise more than one alkanolamine such as a mixture of two or three alkanolamines.

The concentration of at least one alkalizing agent varies between 0.25 and 35%, preferably 1 and 30, more preferably 2.5 and 25 and most preferably 2.5 to 20% by weight calculated to the total composition.

It has also been found out that the anhydrous composition, aqueous oxidizing composition and aqueous alkalizing composition should preferably be mixed at certain ratio in order to guarantee the optimum results. Preferably the compositions are mixed at a weight ratio in the range of anhydrous composition to aqueous oxidizing composition to aqueous alkalizing composition 1:1:1 to 1:10:10, more preferably 1:2:2 to 1:8:8 and most preferably 1:3:3 to 1:5:5.

Any of the above mentioned compositions, composition of the present invention and also the compositions mixed with the composition present invention, can comprise one or more of the substances disclosed below.

The compositions may comprise ceramide type of compound such as cetyl-PG-hydroxyethylpalmitamide.

Further optional ingredient are sterols, especially the phytosterols are useful hair restructuring compounds can be present in the above mentioned compositions. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Furthermore, compositions may comprises at least one diamine compound. Preferred diamide compounds are according to the general structure

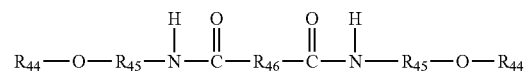

wherein $R_{44}$ is a linear or branched, saturated or unsaturated alkyl chain with 1 to 12 C atoms which may be substituted with hydroxy and/or alkoxy groups, preferably $R_{44}$ is linear or branched, saturated or unsaturated alkyl chain with 1 to 12 C atoms which may be substituted by 1 to 3 substituents selected from a hydroxy group and C1 to C6 alkoxy group, more preferably $R_{44}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{45}$ is linear or branched alkyl chain with 1 to 5 C atoms, preferably linear or branched alkyl chain with 2 to 5 C atoms and more preferably an alkyl chain with 2 to 3 C atoms, and $R_{46}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

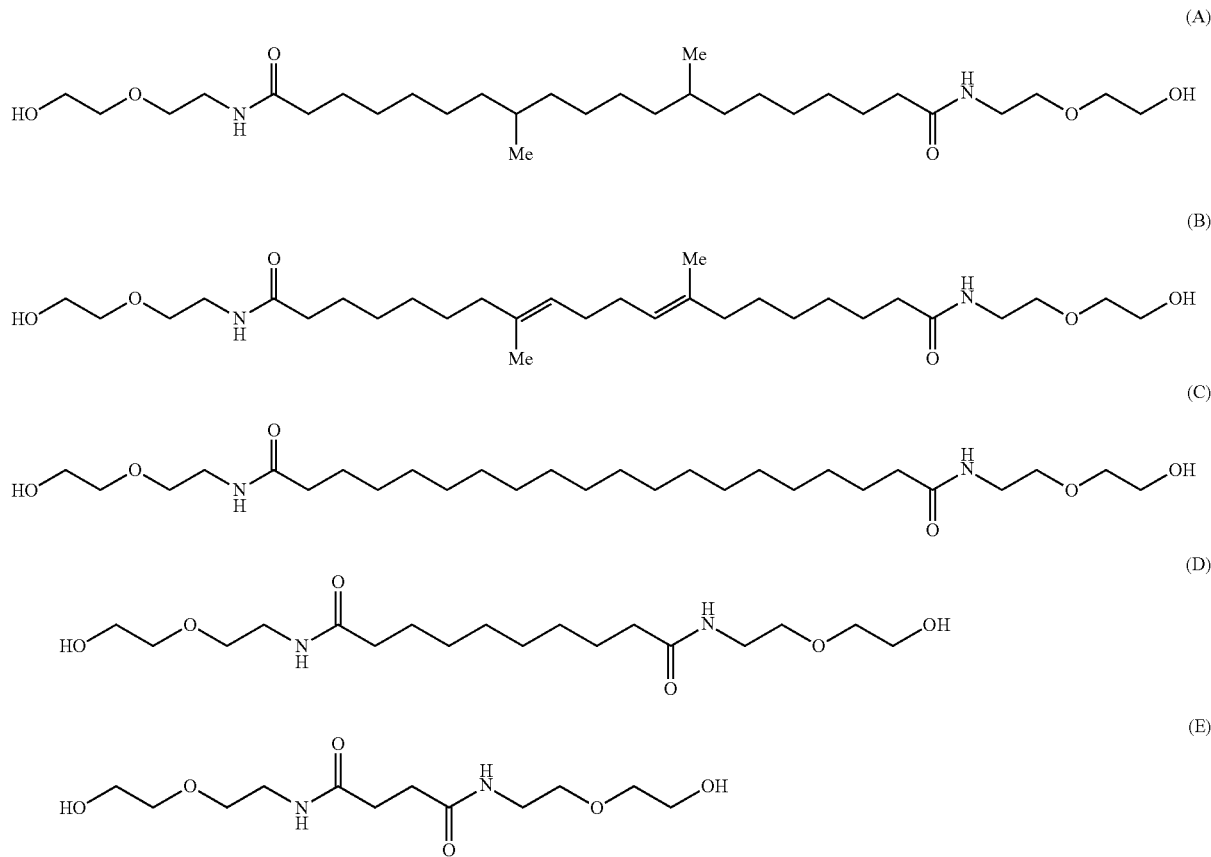

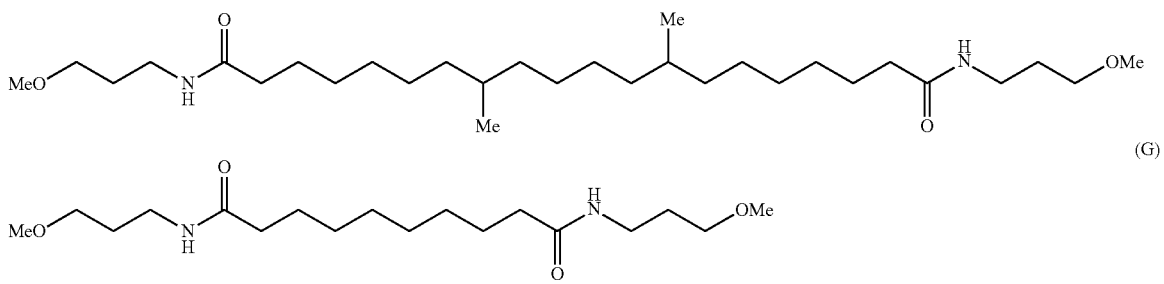

(F)

(G)

Particularly preferred diamide compound is the compound F which is bis (methoxypropylamido) isodocosane and commercially available from Kao Corporation—Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to the total composition.

Further additional compounds may be present in the above mentioned compositions of the present invention is ubichinone of the formula

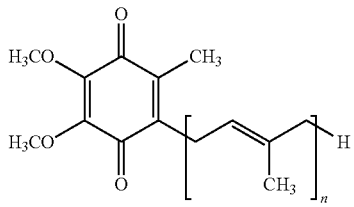

where n is a number between 1 and 10. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to the total composition.

The composition of the present invention may further comprise the compounds found customarily in such compositions such as chelating agents such as EDTA and/or etidronic acid and/or their salts, pH adjusting agents such as organic and/or inorganic acids and/or their salts, preservatives, oxidizing agent stabilizing agents such as acetaminophen and/or salicylic acid, fragrance and additional compounds especially improving hair conditions.

The following examples are to illustrate but not to limit the invention.

EXAMPLE 1

Anhydrous Composition

| | % by weight |
|---|---|
| Soya oil | 40 |
| *Ricinus* oil | 15 |

-continued

| | % by weight |
|---|---|
| Dimethicone 350 cSt | 5 |
| Sodium laureth sulphate | 21 |
| Cocamide DEA | 10 |
| Laureth-4 | 3 |
| Poloxamer 101 | 3 |
| p-Toluenediamine sulphate | 1 |
| Resorcinol | 0.5 |
| Fragrance | 1 |
| Antioxidant | 0.5 |

The above composition was prepared by mixing all components in order and dispersing finally p-toluenediamine sulphate and resorcinol in the mixture.

Aqueous Oxidizing Composition

| | % by weight |
|---|---|
| Cetearyl alcohol | 2.0 |
| Mineral oil | 2.5 |
| Sodium lauryl sulphate | 0.2 |
| Glycerin | 0.9 |
| Hydrogen peroxide | 9.0 |
| Salicylic acid | 0.05 |
| Etidronic acid | 0.2 |
| Phosphoric acid/sodium phosphate | 0.3 |
| Water | to 100 |

Aqueous Alkalizing Composition

| | % by weight |
|---|---|
| Ammonia (25% by weight in water) | 20 |
| Water | 80 |

Ready to use composition was prepared by mixing the below given quantities of the individual composition.

| | By weight |
|---|---|
| Anhydrous composition | 10 |
| Aqueous oxidizing composition | 40 |
| Aqueous alkalizing composition | 40 |

After mixing an emulsion was obtained which appeared to be an opaque liquid with certain consistency. A hair streak comprising partly damaged parts with previous reductive permanent shaping treatment was colored homogeneously in its length.

The following examples are within the scope of the present invention.

EXAMPLE 2

| | % by weight |
|---|---|
| Wheat germ oil | 50 |
| Isopropyl myristate | 5 |
| Phenyl trimethicone | 1 |
| MIPA laureth sulphate | 20 |
| Lauramide MEA | 13 |
| Ceteareth-20 | 2 |
| Poloxamer 101 | 2 |
| 4-amino-m-cresol | 1 |
| 4-amino-2-hydroxytoluene | 0.5 |
| 2-Hydroxyethyl-p-phenylenediamine sulfate | 1 |
| m-aminophenol | 1 |
| Resorcinol | 2 |
| Fragrance | 1 |
| Antioxidant, BHT | 0.5 |

EXAMPLE 3

| | % by weight |
|---|---|
| Wheat germ oil | 40 |
| Paraffin oil | 10 |
| Isopropyl myristate | 5 |
| MIPA laureth sulphate | 16 |
| Lauramide MEA | 15 |
| Ceteareth-20 | 4 |
| Poloxamer 101 | 3 |
| p-Toluenediamine sulphate | 2 |
| 4-amino-m-cresol | 1 |
| 4-amino-2-hydroxytoluene | 1 |
| Resorcinol | 1 |
| Fragrance | 1.5 |
| Antioxidant, BHT | 0.5 |

EXAMPLE 4

| | % by weight |
|---|---|
| Soybean oil | 30 |
| *Ricinus* oil | 10 |
| Isopropylpalmitate | 10 |
| Phenyl trimethicone | 1 |
| Sodium laureth sulphate | 18 |
| Lauramide MEA | 15 |
| Ceteareth-4 | 2 |
| Poloxamer 101 | 3 |
| p-Toluenediamine sulphate | 3 |
| 1-hydroxyethyl-4,5-diaminopyrazol sulphate | 1 |
| 4-amino-m-cresol | 1 |
| 4-amino-2-hydroxytoluene | 1 |
| Resorcinol | 1 |
| Basic red 51 | 1 |
| Fragrance | 1.5 |
| Antioxidant, BHT | 0.5 |

EXAMPLE 5

| | % by weight |
|---|---|
| Almond oil | 30 |
| Dicetyl ether | 10 |
| Paraffin oil | 10 |
| Sodium laureth sulphate | 20 |
| Lauramide MEA | 15 |
| Ceteareth-4 | 2 |
| Poloxamer 101 | 3 |
| p-Toluenediamine sulphate | 3 |
| 1-hydroxyethyl-4,5-diaminopyrazol sulphate | 1 |
| Resorcinol | 2 |
| Basic red 51 | 2 |
| Fragrance | 1.5 |
| Antioxidant, BHT | 0.5 |

EXAMPLE 6

| | % by weight |
|---|---|
| Olive oil | 30 |
| Distearyl ether | 10 |
| *Ricinus* oil | 10 |
| Sodium laureth sulphate | 20 |
| Lauramide MEA | 15 |
| Ceteareth-4 | 3 |
| Poloxamer 101 | 2 |
| p-Toluenediamine sulphate | 4 |
| Resorcinol | 4 |
| Fragrance | 1.5 |
| Antioxidant, BHT | 0.5 |

EXAMPLE 7

| | % by weight |
|---|---|
| Soybean oil | 30 |
| Myristyl myristate | 5 |
| Paraffin oil | 5 |
| Dicetyl ether | 5 |
| *Ricinus* oil | 5 |
| Dimethicone 350 cSt | 5 |
| Sodium laureth sulphate | 15 |
| Lauramide MEA | 16 |
| Ceteareth-4 | 2 |
| Poloxamer 101 | 2 |
| p-Toluenediamine sulphate | 4 |
| Resorcinol | 4 |
| Fragrance | 1.5 |
| Antioxidant, BHT | 0.5 |

EXAMPLE 8

| | % by weight |
|---|---|
| Soybean oil | 30 |
| Myristyl myristate | 5 |
| Paraffin oil | 5 |
| Dicetyl ether | 5 |
| *Ricinus* oil | 5 |
| Dimethicone 350 cSt | 5 |
| Cetrimonium chloride | 15 |
| Lauramide MEA | 15 |

-continued

| | % by weight |
|---|---|
| Ceteareth-4 | 2 |
| Poloxamer 101 | 3 |
| p-Toluenediamine sulphate | 4 |
| Resorcinol | 4 |
| Fragrance | 1.5 |
| Antioxidant, BHT | 0.5 |

EXAMPLE 9

The anhydrous coloring compositions of examples 2 to 8 were also used to colour hair streaks with the following aqueous oxidizing and alkalizing compositions in the same weight ratio as given under example 1 and it was found out that homogeneous and intensive colors were obtained.

Aqueous Oxidizing Composition

| | % by weight |
|---|---|
| Cetearyl alcohol | 5.0 |
| Mineral oil | 1.5 |
| Cetrimonium chloride | 2.0 |
| Glycerin | 0.9 |
| Hydrogen peroxide | 6.0 |
| Salicylic acid | 0.05 |
| Etidronic acid | 0.2 |
| Phosphoric acid/sodium phosphate | 0.3 |
| Water | to 100 |

Aqueous Alkalizing Composition

| | % by weight |
|---|---|
| Monoethanolamine | 13 |
| Water | 87 |

EXAMPLE 10

The same oxidizing composition as in Example 9 but with 12% hydrogen peroxide and the same alkalizing composition as in Example 10 were used in the same weight ratio as in example 1 with examples 2 to 8 and homogeneous and intensive colours were obtained.

The invention claimed is:

1. An anhydrous dyeing composition for hair comprising:
(a) one or more oxidative dye precursors,
(b) one or more oil which is liquid at 20° C.,
(c) at least one anionic surfactant,
(d) at least one nonionic surfactant, and
(e) a surface active block polymer of the general structure

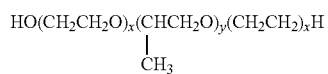

wherein x is a number 4 or more and y is a number 25 or more,
wherein
components (c) and (d) are present at a total concentration in the range of 2% to 40% by weight, calculated to total composition, and
components (a)-(d) and concentrations thereof are selected so that the composition is liquid at 20° C.

2. The composition according to claim 1, wherein the one or more oil is present at a total concentration in the range of 35 to 80% by weight, calculated to the total composition.

3. The composition according to claim 1, wherein the one or more oil is selected from natural oils and synthetic oils.

4. The composition according to claim 1, wherein the one or more oil is a synthetic oil selected from silicones, fatty acid fatty alcohol esters according to the general structure

R50C(O)R51 wherein R50 is a straight or branched, saturated or unsaturated alkyl with 11 to 21 C atoms and R51 is a straight or branched, saturated or unsaturated alkyl with 1 to 22 C atoms, and fatty alcohol ethers according to general structure

R3OR4 wherein R3 and R4 are same or different, straight or branched, saturated or unsaturated alkyl with 8 to 22 C atoms.

5. The composition according to claim 1, wherein the one or more oil is a natural oil selected from mineral oil and plant derived triglycerides.

6. The composition according to claim 1, wherein the one or more oil comprises at least one natural oil and at least one synthetic oil.

7. The composition according to claim 1, wherein the at least one anionic surfactant is selected from alkyl sulphates which are ammonium C12-15 alkyl sulphate, ammonium C12-16 alkyl sulphate, ammonium coco sulphate, ammonium lauryl sulphate, ammonium myristyl sulphate, magnesium coco sulphate, magnesium lauryl sulphate, magnesium coco/TEA sulphate, MEA lauryl sulphate, MIPA lauryl sulphate, potassium lauryl sulphate, sodium caprylyl sulphate, sodium cetearyl sulphate, sodium cetyl sulphate, sodium coco sulphate, sodium decyl sulphate, sodium ethylhexyl sulphate, sodium lauryl sulphate, sodium myristyl sulphate, sodium oleyl sulphate, sodium stearyl sulphate, sodium tridecyl sulphate, TEA coco sulphate, TEA lauryl sulphate, TEA oleyl sulphate and TIPA lauryl sulphate and alkyl ether sulfates which are ammonium coceth sulphate, ammonium laureth sulphate, ammonium myristeth sulphate, magnesium coceth sulphate, magnesium laureth sulphate, MEA laureth sulphate, MIPA laureth sulphate, potassium laureth sulphate, sodium ceteareth sulphate, sodium ceteth sulphate, sodium coceth sulphate, sodium laureth sulphate, sodium myristeth sulphate, sodium oleth sulphate, sodium steareth sulphate, sodium trideceth sulphate, TEA coceth sulphate, TEA laureth sulphate, TEA oleeth sulphate, TIPA laureth sulphate and mixtures thereof, and
the at least one nonionic surfactant is selected from fatty alcohol polyglycol ethers according to general structure R52(OCH2CH2)nOH wherein R52 is straight or branched, saturated or unsaturated alkyl with 8 to 22 C atoms and n is a number between 1 and 50,
alkyl polyglucosides of the general structure R6-O-(R7O)nO-Zx wherein R6 is an alkyl group with 8 to 18 carbon atoms, R7 is an ethylene or propylene group, Z is a saccharide group with 5 to 6 carbon atoms, n is a number from 0 to 10 and x is a number between 1 and 5, and fatty acid mono or dialkanolamides of the general structure

R60C(O)NR61R62 wherein R60 is straight or branched, saturated or unsaturated alkyl with 9 to 21 C atoms, R61 and R62 are same or different H and C1 to C4 alkyl substituted with an OH group which may additionally be branched.

8. The composition according to claim 1, further comprising one or more cationic surfactant of the following general structure

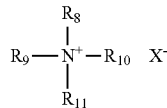

where R8 is a saturated or unsaturated, branched or non-branched alkyl chain with 8-22 C atoms, or R12CONH(CH2)$n$ where R12 is saturated or unsaturated, branched or non-branched alkyl chain with 7-21 C atoms and n has typical value of 1-4, or R13COO(CH2)$n$ where R13 is saturated or unsaturated, branched or non-branched alkyl chain with 7-21 C atoms and n has typical value of 1-4, and
and R9, R10 and R11 are independent from each other H or lower alkyl chain with 1 to 4 carbon atoms, and X is an anion.

9. The composition according to claim 1, which comprises one or more direct dyes selected from cationic, anionic neutral nitro dyes and mixtures thereof.

10. The composition according to claim 1, which comprises one or more phospholipid at a total concentration in the range of 0.1 to 10% by weight calculated to the total composition.

11. A process for dyeing hair comprising:
(a) mixing the composition according to claim 1 with two aqueous compositions wherein one of the two aqueous compositions is an aqueous oxidizing composition comprising at least one oxidizing agent and having a pH in the range of 2 to 6, and the other of the two aqueous compositions is an aqueous alkalizing composition which comprises at least one alkalizing agent, thereby obtaining an emulsion,
(b) applying onto hair the emulsion obtained in step (a),
(c) leaving the emulsion obtained in step (a) on the hair 5 to 45 min, and
(d) rinsing off from hair the emulsion obtained in step (a).

12. The process according to claim 11, wherein the aqueous oxidizing composition is an emulsion and comprises hydrogen peroxide at a concentration in the range of 1 to 20% by weight calculated to the total composition, and the aqueous alkalizing composition comprises at least one alkalizing agent selected from ammonia or ammonium hydroxide and a compound according to the general formula

R43R41R42N wherein R43, R41 and R42 are same or different H, C1-C6 alkyl, C1-C6 monohydroxyalkyl or C2-C6 polyhydroxyalkyl with the condition that at least one of R43, R41 and R42 is a mono or polyhydroxyalkyl.

13. A kit for dyeing hair, comprising three or more compositions wherein one of the three or more compositions is a composition according to claim 1, a second of the three or more compositions is an aqueous composition comprising one or more oxidizing agent and a third of the three or more compositions is an aqueous composition comprising one or more alkalizing agent.

14. The composition of claim 1, further comprising one or more coupling substances.

15. The composition of claim 1, wherein the one or more oil is selected from the group consisting of behenyl behenate, behenyl isostearte, butyl stearate, butyl oleate, butyl myristate, butyloctyl oleate, cetyl palmitate, cetyl myristate, cetyl oleate, cetyl caprylate, cetyl caprate, decyl oleate, decyl cocoate, decyl isostearate, ethylhexyl myristate, ethyl hexyl laurate, ethyl hexyl oleate, ethyl isostearte, ethyl laurate, ethyl linoleate, ethyl myristate, ethyl oleate, ethyl palmitate, ethylricinoleate, ethyl stearate, hexyl isostearet, hexyl laurate, hexyl myristate, hexyl stearate, hexyl decyl oleate, isobutyl laurate, isobutyl myristate, isobutyl palmitate, isobutyl stearate, isocetyl behenate, isobutyl laurate, isobutyl oleate, isobutyl stearate, isobutyl cocoate, isohexyl caprate, isopropyl palmitate, isopropyl stearate, isopropyl behenate, isopropyl laurate, isopropyl oleate, isopropyl ricinoleate, isopropyl palmitate, dicetyl ether, dimyrstyl ether, dicyprylyl etiher, dodecyl ether, ricinus oil, soja oil avocado oil, olive oil, almond oil, peach oil, passiflora oil, black cumin oil, borage oils, evening primrose oil, grape seed oil, hempseed oil, kukui nut oil, rosehip oil, safflower oil, walnut oil and wheat germ oil.

16. The composition of claim 4, wherein the one or more oil is a nonvolatile silicone.

17. The composition of claim 1, wherein the surface active block polymer is present at a concentration in the range of 0.1 to 7.5% by weight calculated to the total composition.

18. The composition of claim 10, wherein the one or more phospholipid is present at a concentration in the range of 0.2 to 7.5% by weight calculated to the total composition.

* * * * *